United States Patent
Onogawa et al.

(10) Patent No.: US 8,338,625 B2
(45) Date of Patent: *Dec. 25, 2012

(54) PROCESS FOR PRODUCTION OF BENZALDEHYDE COMPOUND

(75) Inventors: Yoshio Onogawa, Shizuoka (JP); Kazuyoshi Yamanaka, Shizuoka (JP); Masaji Hirota, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 207 days.

This patent is subject to a terminal disclaimer.

(21) Appl. No.: 12/997,900

(22) PCT Filed: Jun. 9, 2009

(86) PCT No.: PCT/JP2009/060817
§ 371 (c)(1),
(2), (4) Date: Dec. 14, 2010

(87) PCT Pub. No.: WO2009/154154
PCT Pub. Date: Dec. 23, 2009

(65) Prior Publication Data
US 2011/0098489 A1 Apr. 28, 2011

(30) Foreign Application Priority Data
Jun. 16, 2008 (JP) .................. 2008-157213

(51) Int. Cl.
*C07D 317/18* (2006.01)
(52) U.S. Cl. ...................................... 549/453
(58) Field of Classification Search .................. 549/453
See application file for complete search history.

(56) References Cited

U.S. PATENT DOCUMENTS 5,145,980 A 9/1992 Wenderoth et al.

FOREIGN PATENT DOCUMENTS

| JP | 56-166131 A | 12/1981 |
| JP | 09-095462 A | 4/1997 |
| JP | 2007-176799 A | 7/2007 |

OTHER PUBLICATIONS

T. Giannopoulos et al., "Tele Nucleophilic Aromatic Substitutions in 1-Nitro-3- and 1,3-Dinitro-5-trichloromethylbenzene, and 3-Trichloromethylbenzonitrile. A New Synthesis of the 1,4-Benzothiazine-3(4H)-one Ring System from 3-Nitrobenzoic Acid", Tetrahedron, vol. 56, pp. 447-453, (2000).
Int'l Search Report issued on Jul. 7, 2009 in Int'l Application No. PCT/JP2009/060817.
Int'l Preliminary Report on Patentability dated Jan. 20, 2011 in Int'l Application No. PCT/JP2009/060817.

*Primary Examiner* — Taofiq A Solola
(74) *Attorney, Agent, or Firm* — Panitch Schwarze Belisario & Nadel LLP

(57) ABSTRACT

A method of producing a corresponding acetal compound which comprises reacting a benzal halide compound represented by formula (1)

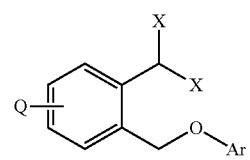

(1)

(wherein, Q represents a hydrogen atom or a halogen atom, X represents a halogen atom, and Ar represents a phenyl group optionally substituted with at least one group selected from the group consisting of alkyl groups having 1 to 4 carbon atoms and halogen atoms.) and an alcohol compound in the presence of at least one alkaline earth metal compound selected from the group consisting of alkaline earth metal oxides, alkaline earth metal hydroxides and alkaline earth metal carbonates.

16 Claims, No Drawings

PROCESS FOR PRODUCTION OF BENZALDEHYDE COMPOUND

CROSS-REFERENCE TO RELATED APPLICATIONS

This application is a Section 371 of International Application No. PCT/JP2009/060817, filed Jun. 9, 2009, which was published in the Japanese language on Dec. 23, 2009, under International Publication No. WO 2009/154154 A1 and the disclosure of which is incorporated herein by reference.

BACKGROUND OF THE INVENTION

The present invention relates to a method of producing a benzaldehyde compound.

A benzaldehyde compound represented by formula (3)

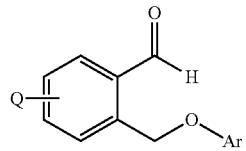
(3)

(wherein, Q represents a hydrogen atom or a halogen atom, and Ar represents a phenyl group optionally substituted with at least one group selected from the group consisting of alkyl groups having 1 to 4 carbon atoms and halogen atoms.) is useful as a production intermediate of a bactericide (see, e.g., JP-A No. 9-95462 and U.S. Pat. No. 5,145,980).

As the method of producing a benzaldehyde compound represented by formula (3), a method comprising oxidation of the corresponding benzyl halide compound is disclosed in JP-A No. 9-95462, and a method comprising reduction of the corresponding benzonitrile compound is disclosed in U.S. Pat. No. 5,145,980.

BRIEF SUMMARY OF THE INVENTION

The present invention relates to:

1) A method of producing a corresponding acetal compound which comprises reacting a benzal halide compound represented by formula (1)

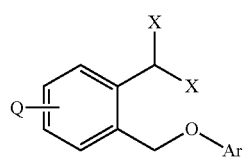
(1)

(wherein, Q represents a hydrogen atom or a halogen atom, X represents a halogen atom, and Ar represents a phenyl group optionally substituted with at least one group selected from the group consisting of alkyl groups having 1 to 4 carbon atoms and halogen atoms.) and an alcohol compound in the presence of at least one alkaline earth metal compound selected from the group consisting of alkaline earth metal oxides, alkaline earth metal hydroxides and alkaline earth metal carbonates.

2) The production method according to 1), wherein the alcohol compound is a monohydric alcohol compound having 1 to 6 carbon atoms or a dihydric alcohol compound having 2 to 6 carbon atoms.

3) The production method according to 1), wherein the alcohol compound is a dihydric alcohol compound having 2 to 6 carbon atoms.

4) The production method according to 3), wherein the dihydric alcohol compound is a 1,2-diol compound.

5) The production method according to 4), wherein the 1,2-diol compound is ethylene glycol.

6) The production method according to any one of 1) to 5), wherein the alkaline earth metal is calcium.

7) The production method according to any one of 1) to 5), wherein the alkaline earth metal compound is an alkaline earth metal carbonate.

8) The production method according to 7), wherein the alkaline earth metal carbonate is calcium carbonate.

9) The production method according to any one of 1) to 8), wherein X represents a chlorine atom.

10) The production method according to any one of 1) to 9), wherein Ar represents a phenyl group substituted with at least one alkyl group having 1 to 4 carbon atoms.

11) The production method according to 10), wherein the phenyl group substituted with at least one alkyl group having 1 to 4 carbon atoms is 2,5-dimethylphenyl group.

12) A method of producing a benzaldehyde compound represented by formula (3)

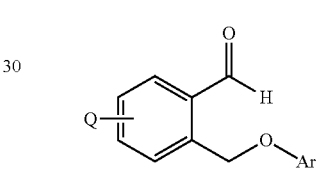
(3)

(wherein Q and Ar represent respectively the same meaning as described above.) which comprises obtaining an acetal compound by the production method according to any one of 1) to 11), and reacting the resultant acetal compound and water in the presence of an acid.

13) The production method according to 12), wherein the acid is a Bronsted acid.

14) The production method according to 13), wherein the Bronsted acid is hydrochloric acid.

15) The production method according to any one of 1) to 14), wherein the benzal halide compound represented by formula (1) is a benzal halide compound obtained by reacting a compound represented by formula (4)

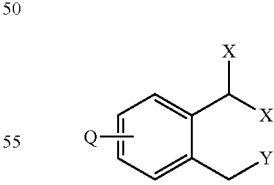
(4)

(wherein, Q and X represent respectively the same meaning as described above, and Y represents a halogen atom.) and a phenol compound represented by formula (5)

Ar—OH (5)

(wherein, Ar represents the same meaning as described above.) in the presence of a base.

16) 2-(2,5-dimethylphenoxymethyl)benzaldehyde ethylene glycol acetal.

DETAILED DESCRIPTION OF THE INVENTION

A benzaldehyde compound represented by formula (3) (hereinafter, briefly referred to as benzaldehyde compound (3))

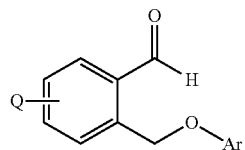

(3)

(wherein, Q represents a hydrogen atom or a halogen atom, and Ar represents a phenyl group optionally substituted with at least one group selected from the group consisting of alkyl groups having 1 to 4 carbon atoms and halogen atoms.) can be produced by reacting a benzal halide compound represented by formula (1) (hereinafter, briefly referred to as benzal halide compound(1))

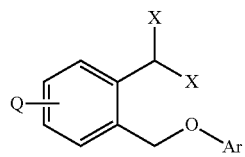

(1)

(wherein, Q and Ar represent the same meaning as described above, and X represents a halogen atom.) and an alcohol compound in the presence of at least one alkaline earth metal compound selected from the group consisting of alkaline earth metal oxides, alkaline earth metal hydroxides and alkaline earth metal carbonates, to obtain the corresponding acetal compound, and reacting the resultant acetal compound and water in the presence of an acid.

In the above-described formula, Q represents a hydrogen atom or a halogen atom, preferably a hydrogen atom. The halogen atom represented by Q includes a fluorine atom, chlorine atom, bromine atom and iodine atom.

In the above-described formula, Ar represents a phenyl group optionally substituted with at least one selected from the group consisting of alkyl groups having 1 to 4 carbon atoms and halogen atoms. The alkyl group having 1 to 4 carbon atoms includes a methyl group, ethyl group, propyl group, isopropyl group, butyl group, isobutyl group and tert-butyl group, and the halogen atom includes a fluorine atom and chlorine atom. As such substituents, alkyl groups having 1 to 4 carbon atoms are preferable. The number of the substituent is preferably 1 to 3, more preferably 1 or 2, particularly preferably 2.

The phenyl group optionally substituted with at least one selected from the group consisting of alkyl groups having 1 to 4 carbon atoms and halogen atoms includes a phenyl group, 2-methylphenyl group, 4-methylphenyl group, 5-methylphenyl group, 2,5-dimethylphenyl group, 2,4-dimethylphenyl group, 2,6-dimethylphenyl group, 2,4,6-trimethylphenyl group, 2-ethylphenyl group, 4-ethylphenyl group, 5-ethylphenyl group, 2,5-diethylphenyl group, 2,4-diethylphenyl group, 2,6-diethylphenyl group, 2,4,6-triethylphenyl group, 2-propylphenyl group, 4-propylphenyl group, 5-propylphenyl group, 2,5-dipropylphenyl group, 2,4-dipropylphenyl group, 2,6-dipropylphenyl group, 2,4,6-tripropylphenyl group, 2-isopropylphenyl group, 4-isopropylphenyl group, 5-isopropylphenyl group, 2,5-isopropylphenyl group, 2,4-diisopropylphenyl group, 2,6-diisopropylphenyl group, 2,4,6-triisopropylphenyl group, 2-butylphenyl group, 4-butylphenyl group, 5-butylphenyl group, 2,5-dibutylphenyl group, 2,4-dibutylphenyl group, 2,6-dibutylphenyl group, 2,4,6-tributylphenyl group, 2-isobutylphenyl group, 4-isobutylphenyl group, 5-isobutylphenyl group, 2,5-diisobutylphenyl group, 2,4-diisobutylphenyl group, 2,6-diisobutylphenyl group, 2,4,6-triisobutylphenyl group, 2-tert-butylphenyl group, 4-tert-butylphenyl group, 5-tert-butylphenyl group, 2,5-di-tert-butylphenyl group, 2,4-di-tert-butylphenyl group, 2,6-di-tert-butylphenyl group, 2,4,6-tri-tert-butylphenyl group, 2-fluorophenyl group, 4-fluorophenyl group, 2,4-difluorophenyl group, 2,4,6-trifluorophenyl group, pentafluorophenyl group, 2-chlorophenyl group, 4-chlorophenyl group, 2,4-dichlorophenyl group, 2,4,6-trichlorophenyl group, and pentachlorophenyl group. Of them, phenyl groups substituted with at least one alkyl group having 1 to 4 carbon atoms are preferable, 2-methylphenyl group and 2,5-dimethylphenyl group are more preferable, 2,5-dimethylphenyl group is particularly preferable.

In the above-described formula (1), the halogen atom represented by X includes a chlorine atom, bromine atom and iodine atom, and a chlorine atom is preferable from the standpoint of cost.

The benzal halide compound (1) includes 2-(phenoxymethyl)benzal chloride, 2-(2-methylphenoxymethyl)benzal chloride, 2-(2-ethylphenoxymethyl)benzal chloride, 2-(2-isopropylphenoxymethyl)benzal chloride, 2-(4-methylphenoxymethyl)benzal chloride, 2-(4-isopropylphenoxymethyl) benzal chloride, 2-(2,5-dimethylphenoxymethyl)benzal chloride, 2-(2,5-diethylphenoxymethyl)benzal chloride, 2-(2,5-diisopropylphenoxymethyl)benzal chloride, 2-(2,4,5-trimethylphenoxymethyl)benzal chloride, 2-(2,4,6-trimethylphenoxymethyl)benzal chloride, 2-(3,4,5-trimethylphenoxymethyl)benzal chloride, 2-(2,4,5-trimethylphenoxymethyl)benzal chloride, 2-(2,5-dimethylphenoxymethyl)-3-chloro benzal chloride, 2-(2,5-dimethylphenoxymethyl)-4-chloro benzal chloride, 2-(2,5-dimethylphenoxymethyl)-5-chloro benzal chloride, 2-(2,5-dimethylphenoxymethyl)-6-chloro benzal chloride, 2-(2,5-diethylphenoxymethyl)-3-chloro benzal chloride, 2-(2,5-diethylphenoxymethyl)-4-chloro benzal chloride, 2-(2,5-diethylphenoxymethyl)-5-chloro benzal chloride, 2-(2,5-diethylphenoxymethyl)-6-chloro benzal chloride, 2-(2,5-diisopropylphenoxymethyl)-3-chloro benzal chloride, 2-(2,5-diisopropylphenoxymethyl)-4-chloro benzal chloride, 2-(2,5-diisopropylphenoxymethyl)-5-chloro benzal chloride, 2-(2,5-diisopropylphenoxymethyl)-6-chloro benzal chloride, 2-(2,5-diethylphenoxymethyl)benzal bromide, 2-(2,5-diethylphenoxymethyl)benzal iodide, 2-(2,5-dimethylphenoxymethyl)-4-bromo benzal bromide, 2-(2,5-diethylphenoxymethyl)-4-bromo benzal bromide, 2-(2,5-diisopropylphenoxymethyl)-4-bromo benzal bromide and 2-(2,5-dimethylphenoxymethyl)-4-iodo benzal iodide.

The alcohol compound may advantageously be one having one or more alcoholic hydroxyl groups in the molecule, and monohydric alcohol compounds having 1 to 6 carbon atoms and dihydric alcohol compounds having 2 to 6 carbon atoms are preferable.

The monohydric alcohol compound having 1 to 6 carbon atoms includes monohydric alcohol compounds represented by formula (10)

R—OH (10)

(wherein, R represents an alkyl group having 1 to 6 carbon atoms), and the alkyl group having 1 to 6 carbon atoms includes a methyl group, ethyl group, 1-propyl group, 2-propyl group, 1-butyl group, 2-butyl group and tert-butyl group.

The dihydric alcohol compound having 2 to 6 carbon atoms includes dihydric alcohol compounds represented by formula (11)

(wherein, R' represents an alkylene group having 2 to 6 carbon atoms), and the alkylene group having 2 to 6 carbon atoms includes an ethylene group, trimethylene group, tetramethylene group and 2,3-dimethyl-1,4-butylene group.

The monohydric alcohol compound having 1 to 6 carbon atoms includes methanol, ethanol, 1-propanol, 2-propanol, 1-butanol, 2-butanol and 2-methyl-2-propanol. The dihydric alcohol compound having 2 to 6 carbon atoms includes ethylene glycol, propylene glycol and pinacol. Alcohol compounds other than these compounds include tri-hydric alcohol compounds such as glycerin.

As such alcohol compounds, dihydric alcohol compounds having 2 to 6 carbon atoms are preferable, 1,2-diol compounds are more preferable, ethylene glycol is particularly preferable.

The use amount of the alcohol compound is not restricted, and the alcohol compound may be used in a large excess amount simultaneously as a solvent, and in the case of use of a monohydric alcohol compound, the use amount is usually 2 to 200 mol, preferably 2 to 20 mol with respect to 1 mol of benzal halide compound (1), and in the case of use of a di or more-hydric alcohol compound, the use amount is usually 1 to 100 mol, preferably 1 to 10 mol with respect to 1 mol of benzal halide compound (1).

The reaction of benzal halide compound (1) with an alcohol compound is carried out in the presence of at least one alkaline earth metal compound selected from the group consisting of alkaline earth metal oxides, alkaline earth metal hydroxides and alkaline earth metal carbonates. The alkaline earth metal includes magnesium, calcium and barium, and calcium is preferable from the standpoint of the price of the alkaline earth metal compound. The alkaline earth metal oxide includes magnesium oxide. The alkaline earth metal hydroxide includes calcium hydroxide and barium hydroxide. The alkaline earth metal carbonate includes calcium carbonate and barium carbonate. Of them, alkaline earth metal carbonates are preferable, calcium carbonate is more preferable.

The use amount of the alkaline earth metal compound is usually 1 to 10 mol, preferably 1 to 4 mol with respect to 1 mol of benzal halide compound (1).

The reaction of benzal halide compound (1) with an alcohol compound may be carried out without solvent, or may be carried out in the presence of a solvent. The solvent includes aromatic hydrocarbon solvents such as xylene, toluene and benzene, aliphatic hydrocarbon solvents such as pentane, hexane, heptanes and cyclohexane, ether solvents such as tetrahydrofuran, diethyl ether, tert-butyl methyl ether and cyclopentyl methyl ether. As described above, the alcohol compounds may be used simultaneously as a solvent. These may be used singly, or in admixture of two or more. It is preferable that the alcohol compound is used as a solvent.

The use amount of the solvent is not restricted, and the use amount is usually 100 parts by weight or less with respect to 1 part by weight of a benzal halide (1) from the standpoint of economy.

The reaction of benzal halide compound (1) with an alcohol compound may be carried out in the presence of a phase transfer catalyst. By this, the reaction can be progressed more smoothly. The phase transfer catalyst includes quaternary ammonium salts such as tetra-n-butyl ammonium bromide, benzyl triethyl ammonium chloride, tetra-n-butyl ammonium hydrogen sulfate and trioctyl methyl ammonium chloride, phosphonium salts such as triphenylphosphine bromide, polyether compounds such as 18-crown-6 and polyethylene glycol.

As the phase transfer catalyst, commercially available ones are usually used.

The use amount of the phase transfer catalyst is usually 0.01 mol or more, preferably 0.05 to 1 mol with respect to 1 mol of benzal halide compound (1).

The reaction temperature is usually −5° C. or more and not more than the boiling point of a solvent, preferably 10 to 200° C. The reaction time is usually 1 to 100 hours.

The reaction is carried out by mixing benzal halide compound (1), an alcohol compound and an alkaline earth metal compound. The mixing order of them is not restricted, and for example, a method which comprises adding benzal halide compound (1) and an alkaline earth metal compound to an alcohol compound is mentioned.

The reaction may be carried out under normal pressure, or may be carried out under pressure.

The progress of the reaction can be confirmed by usual analysis means such as gas chromatography, high performance liquid chromatography and NMR.

Thus, a reaction mixture containing the corresponding acetal compound is obtained, and for example, the acetal compound can be taken out by concentrating the reaction mixture itself or washing the reaction mixture with water before concentration. Further, for example, the acetal compound can also be taken out by purifying the resultant reaction mixture by silica gel chromatography. The taken out acetal compound may be further purified by usual purification means such as re-crystallization, distillation and column chromatography.

In the case of use of a monohydric alcohol compound represented by formula (10) as the alcohol compound, an acetal compound represented by formula (20)

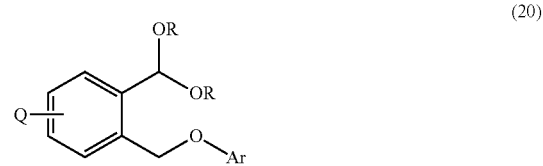

(wherein, R, Q and Ar represent the same meaning as described above.) is obtained as the corresponding acetal compound.

In the case of use of a dihydric alcohol compound represented by formula (11) as the alcohol compound, an acetal compound represented by formula (21)

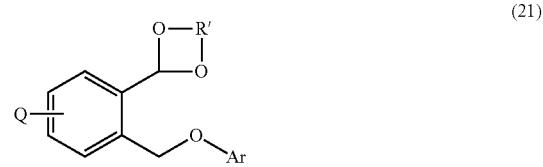

(wherein, R', Q and Ar represent the same meaning as described above.)

is obtained as the corresponding acetal compound.

Thus obtainable acetal compound includes 2-(phenoxymethyl)benzaldehyde ethylene glycol acetal, 2-(2-methylphenoxymethyl)benzaldehyde ethylene glycol acetal, 2-(3-methylphenoxymethyl)benzaldehyde ethylene glycol acetal, 2-(4-methylphenoxymethyl)benzaldehyde ethylene glycol acetal, 2-(2-ethylphenoxymethyl)benzaldehyde ethylene glycol acetal, 2-(4-ethylphenoxymethyl)benzaldehyde ethylene glycol acetal, 2-(2-isopropylphenoxymethyl)benzaldehyde ethylene glycol acetal, 2-(4-isopropylphenoxymethyl)benzaldehyde ethylene glycol acetal, 2-(2-t-butylphenoxymethyl)benzaldehyde ethylene glycol acetal, 2-(4-t-butylphenoxymethyl)benzaldehyde ethylene glycol acetal, 2-(2,4-dimethylphenoxymethyl)benzaldehyde ethylene glycol acetal, 2-(2,5-dimethylphenoxymethyl)benzaldehyde ethylene glycol acetal, 2-(2,6-dimethylphenoxymethyl)benzaldehyde ethylene glycol acetal, 2-(3,5-dimethylphenoxymethyl)benzaldehyde ethylene glycol acetal, 2-(2,4-diethylphenoxymethyl)benzaldehyde ethylene glycol acetal, 2-(2,5-diethylphenoxymethyl)benzaldehyde ethylene glycol acetal, 2-(2,6-diethylphenoxymethyl)benzaldehyde ethylene glycol acetal, 2-(2,5-diisopropylphenoxymethyl)benzaldehyde ethylene glycol acetal, 2-(2,6-diisopropylphenoxymethyl)benzaldehyde ethylene glycol acetal, 2-(2,4,5-trimethylphenoxymethyl)benzaldehyde ethylene glycol acetal, 2-(2,4,6-trimethylphenoxymethyl)benzaldehyde ethylene glycolacetal, 2-(3,4,5-trimethylphenoxymethyl)benzaldehyde ethylene glycolacetal, 2-(2,5-dimethylphenoxymethyl)-3-chloro benzaldehyde ethylene glycolacetal, 2-(2-methylphenoxymethyl)-3-chloro benzaldehyde ethylene glycolacetal, 2-(2,5-dimethylphenoxymethyl)-4-chloro benzaldehyde ethylene glycolacetal, 2-(2-methylphenoxymethyl)-4-chloro benzaldehyde ethylene glycolacetal, 2-(2,5-dimethylphenoxymethyl)-5-chloro benzaldehyde ethylene glycolacetal, 2-(2-methylphenoxymethyl)-5-chloro benzaldehyde ethylene glycolacetal, 2-(2,5-dimethylphenoxymethyl)-6-chloro benzaldehyde ethylene glycolacetal, 2-(2-methylphenoxymethyl)-6-chloro benzaldehyde ethylene glycolacetal, 2-(2,5-diethylphenoxymethyl)-4-chloro benzaldehyde ethylene glycolacetal, 2-(2-ethylphenoxymethyl)-4-chloro benzaldehyde ethylene glycolacetal, 2-(2,5-diisopropylphenoxymethyl)-4-chloro benzaldehyde ethylene glycolacetal, 2-(2-isopropylphenoxymethyl)-4-chloro benzaldehyde ethylene glycolacetal, 2-(2,5-dimethylphenoxymethyl)-4-bromo benzaldehyde ethylene glycolacetal, 2-(2-methylphenoxymethyl)-4-bromo benzaldehyde ethylene glycolacetal, 2-(2,5-dimethylphenoxymethyl)-4-iodo benzaldehyde ethylene glycolacetal, 2-(2-methylphenoxymethyl)-4-iodo benzaldehyde ethylene glycolacetal, 2-(2-methylphenoxymethyl)benzaldehyde dimethylacetal, 2-(2,5-dimethylphenoxymethyl)benzaldehyde dimethylacetal, 2-(2-methylphenoxymethyl)benzaldehyde diethylacetal, 2-(2,5-dimethylphenoxymethyl)benzaldehyde diethylacetal, 2-(2-methylphenoxymethyl)benzaldehyde di(n-propyl)acetal, 2-(2,5-dimethylphenoxymethyl)benzaldehyde di(n-propyl)acetal, 2-(2-methylphenoxymethyl)benzaldehyde diisopropylacetal, 2-(2,5-dimethylphenoxymethyl)benzaldehyde diisopropylacetal, 2-(2-methylphenoxymethyl)benzaldehyde di(n-butyl)acetal, 2-(2,5-dimethylphenoxymethyl)benzaldehyde di(n-butyl)acetal, 2-(2-methylphenoxymethyl)benzaldehyde pinacolacetal, 2-(2,5-dimethylphenoxymethyl)benzaldehyde pinacolacetal, 2-(2-methylphenoxymethyl)benzaldehyde propylene glycolacetal, and 2-(2,5-dimethylphenoxymethyl)benzaldehyde propylene glycolacetal. Of them, 2-(2-methylphenoxymethyl)benzaldehyde ethylene glycolacetal, 2-(2,5-dimethylphenoxymethyl)benzaldehyde ethylene glycolacetal are preferable, 2-(2,5-dimethylphenoxymethyl) benzaldehyde ethylene glycolacetal is more preferable.

The taken out acetal compound and water can be reacted in the presence of an acid to obtain benzaldehyde compound (3). The reaction mixture containing an acetal compound may be used as it is for the reaction with water. The reaction mixture may be washed with water to remove alkaline earth metal compounds and alcohol compounds remaining in the reaction mixture, followed by using for the reaction with water. In the case of washing of the reaction mixture with water, water-insoluble organic solvents such as aromatic hydrocarbon solvents such as xylene, toluene and benzene, aliphatic hydrocarbon solvents such as pentane, hexane, heptanes and cyclohexane may be added, if necessary.

The reaction of the acetal compound with water is carried out in the presence of an acid, and the acid includes Bronsted acids such as hydrochloric acid, sulfuric acid and nitric acid. Of them, hydrochloric acid and sulfuric acid are preferable, hydrochloric acid is more preferable. As the acids, commercially available ones are usually used. If necessary, the acid may be diluted with water or an organic solvent described later before use, or may be concentrated before use. The acid is used usually in the form of an aqueous solution.

The use amount of the acid is usually 0.01 mol or more, preferably 1 to 5 mol with respect to 1 mol of the acetal compound.

The use amount of water is usually 2 mol or more with respect to 1 mol of the acetal compound, its upper limit is not restricted, and water may also be used in a large excess amount simultaneously as a solvent.

The reaction of the acetal compound with water is carried out usually in the presence of an organic solvent. The organic solvent includes aromatic hydrocarbon solvents such as xylene, toluene and benzene, aliphatic hydrocarbon solvents such as pentane, hexane, heptane and cyclohexane, ether solvents such as diethyl ether, tert-butyl methyl ether and cyclopentyl methyl ether, alcohol solvents such as methanol, ethanol, butanol, isopropanol, isobutanol and tert-butanol, aromatic hydrocarbon solvents are preferable, xylene and toluene are more preferable. These organic solvents may be used singly or in admixture of two or more. The use amount of the organic solvent is not restricted, and usually 100 parts by weight or less with respect to 1 part by weight of the acetal compound from the standpoint of economy.

The reaction temperature is usually 1° C. or more and not more than the boiling point of a solvent, preferably 10 to 200° C. The reaction time is usually 1 to 100 hours.

The reaction may be carried out under normal pressure, or may be carried out under pressure.

The progress of the reaction can be confirmed by usual analysis means such as gas chromatography, high performance liquid chromatography, thin layer chromatography and NMR.

The reaction is carried out by mixing an acid, an acetal compound and water, and the mixing order of them is not restricted.

Thus, a reaction mixture containing benzaldehyde compound (3) is obtained, and for example, the benzaldehyde compound (3) can be taken out by concentrating the reaction mixture itself or washing the reaction mixture with water before concentration. The taken out benzaldehyde compound (3) may be further purified by usual purification means such as re-crystallization, distillation and column chromatography.

The benzaldehyde compound (3) includes 2-(phenoxymethyl)benzaldehyde, 2-(2-methylphenoxymethyl)benzaldehyde, 2-(3-methylphenoxymethyl)benzaldehyde, 2-(4-methylphenoxymethyl)benzaldehyde, 2-(2-ethylphenoxymethyl)benzaldehyde, 2-(4-ethylphenoxymethyl)benzaldehyde, 2-(2-isopropylphenoxymethyl)benzaldehyde, 2-(4-isopropylphenoxymethyl)benzaldehyde, 2-(2-tert-butylphenoxymethyl)benzaldehyde, 2-(4-tert-butylphenoxymethyl)benzaldehyde, 2-(2,4-dimethylphenoxymethyl)benzaldehyde, 2-(2,5-dimethylphenoxymethyl)benzaldehyde, 2-(2,6-dimethylphenoxymethyl)benzaldehyde, 2-(3,5-dimethylphenoxymethyl)benzaldehyde, 2-(2,4-diethylphenoxymethyl)benzaldehyde, 2-(2,5-diethylphenoxymethyl)benzaldehyde, 2-(2,6-diethylphenoxymethyl)benzaldehyde, 2-(2,5-diisopropylphenoxymethyl)benzaldehyde, 2-(2,6-diisopropylphenoxymethyl)benzaldehyde, 2-(2,4,5-trimethylphenoxymethyl)benzaldehyde, 2-(2,4,6-trimethylphenoxymethyl)benzaldehyde, 2-(3,4,5-trimethylphenoxymethyl)benzaldehyde, 2-(2,5-dimethylphenoxymethyl)-3-chlorobenzaldehyde, 2-(2-methylphenoxymethyl)-3-chlorobenzaldehyde, 2-(2,5-dimethylphenoxymethyl)-4-chlorobenzaldehyde, 2-(2-methylphenoxymethyl)-4-chlorobenzaldehyde, 2-(2,5-dimethylphenoxymethyl)-5-chlorobenzaldehyde, 2-(2-methylphenoxymethyl)-5-chlorobenzaldehyde, 2-(2,5-dimethylphenoxymethyl)-6-chlorobenzaldehyde, 2-(2-methylphenoxymethyl)-6-chlorobenzaldehyde, 2-(2,5-diethylphenoxymethyl)-4-chlorobenzaldehyde, 2-(2-ethylphenoxymethyl)-4-chlorobenzaldehyde, 2-(2,5-diisopropylphenoxymethyl)-4-chlorobenzaldehyde, 2-(2-isopropylphenoxymethyl)-4-chlorobenzaldehyde, 2-(2,5-dimethylphenoxymethyl)-4-bromobenzaldehyde, 2-(2-methylphenoxymethyl)-4-bromobenzaldehyde, 2-(2,5-dimethylphenoxymethyl)-4-iodobenzaldehyde and 2-(2-methylphenoxymethyl)-4-iodobenzaldehyde. Of them, 2-(2-methylphenoxymethyl)benzaldehyde, 2-(2,5-dimethylphenoxymethyl)benzaldehyde are preferable, 2-(2,5-dimethylphenoxymethyl)benzaldehyde is more preferable.

The benzal halide compound (1) can be produced by reacting a compound represented by formula (4) (hereinafter, briefly referred to as compound (4))

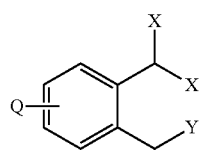

(4)

(wherein, Q and X represent the same meaning as described above, and Y represents a halogen atom.) and a phenol compound represented by formula (5) (hereinafter, briefly referred to as phenol compound (5))

Ar—OH      (5)

(wherein, Ar represents the same meaning as described above.) in the presence of a base.

In the above-described formula (4), the halogen atom represented by Y includes a chlorine atom, bromine atom and iodine atom, and a chlorine atom is preferable from the standpoint of cost. It is preferable that X and Y are identical in the formula (4).

The compound (4) includes 2-(chloromethyl)benzal chloride, 2-(bromomethyl)benzal bromide, 2-(iodomethyl)benzal iodide, 3-chloro-2-(chloromethyl)benzal chloride, 4-chloro-2-(chloromethyl)benzal chloride, 4-bromo-2-(bromomethyl)benzal bromide, 4-iodo-2-(iodomethyl)benzal iodide, 5-chloro-2-(chloromethyl)benzal chloride, 5-bromo-2-(bromomethyl)benzal bromide, 5-iodo-2-(iodomethyl)benzal iodide and 6-chloro-2-(chloromethyl)benzal chloride. 2-(chloromethyl)benzal chloride is preferable from the standpoint of availability.

As the compound (4), commercially available ones may be used, and those produced according to known methods such as a method of reacting an o-xylene compound and a halogen in the presence of a radical initiator or under light irradiation (see, JP-A No. 2006-335737), and other methods may be used.

The phenol compound (5) includes phenol, 2-methylphenol, 2-ethylphenol, 2-isopropylphenol, 4-methylphenol, 4-isopropylphenol, 2,5-dimethylphenol, 2,5-diethylphenol, 2,5-diisopropylphenol, 2,4,5-trimethylphenol, 2,4,6-trimethylphenol, 3,4,5-trimethylphenol, 2-chlorophenol, 4-chlorophenol, 2-fluorophenol, 4-fluorophenol, 2,4-difluorophenol and 2,4,6-trifluorophenol. Of them, 2-methylphenol, 2,5-dimethylphenol are preferable, 2,5-dimethylphenol is more preferable.

As the phenol compound (5), commercially available ones may be used, and those produced by known methods described in J. Am. Chem. Soc., 128, 10694 (2006) or Tetrahedron Letters, 30, 5215 (1989), JP-A No. 2002-3426, may be used.

The phenol compound (5) may be used in an excess amount (for example, 10 mol or more) with respect to the compound (4), or the compound (4) may be used in an excess amount (for example, 10 mol or more) with respect to the phenol compound (5). Preferably, the phenol compound (5) is used in an amount of 0.1 to 10 mol, more preferably 1 to 3 mol with respect to 1 mol of the compound (4).

The base includes tertiary amines such as trimethylamine, triethylamine and diisopropylethylamine; metal alkoxides such as sodium methoxide, sodium ethoxide and potassium tert-butoxide; alkali metal hydroxides such as lithium hydroxide, sodium hydroxide and potassium hydroxide; alkali metal hydride compounds such as sodium hydride, potassium hydride and lithium hydroxide; alkali metal carbonates such as sodium carbonate, potassium carbonate and lithium carbonate; alkali metal hydrogen carbonates such as sodium hydrogen carbonate, potassium hydrogen carbonate and lithium hydrogen carbonate. Alkali metal hydroxides are preferable, sodium hydroxide is more preferable. As the base, commercially available ones are usually used as they are. The base may be diluted with water or a solvent described later.

The use amount of the base is usually 1 mol or more with respect to 1 mol of either compound (4) or phenol compound (5) which is used in the smaller amount, and though there is no upper limit, the use amount is preferably 1 to 3 mol.

The reaction of a compound (4) and a phenol compound (6) is usually carried out in the presence of a solvent. The solvent includes aromatic hydrocarbon solvents such as xylene, toluene and benzene; aliphatic hydrocarbon solvents such as pentane, hexane, heptane and cyclohexane; ether solvents such as tetrahydrofuran, diethyl ether, tert-butyl methyl ether and cyclopentyl methyl ether; nitrile solvents such as acetonitrile and propionitrile; ketone solvents such as tert-butyl methyl ketone; amide solvents such as N,N-dimethylformamide; sulfoxides solvents such as dimethyl sulfoxide; and water. These solvents may be used singly or in admixture of two or more.

The use amount of the solvent is not restricted, and usually 100 parts by weight or less with respect to 1 part by weight of compound (4) from the standpoint of economy.

The reaction of compound (4) with phenol compound (5) is preferably carried out in the presence of a phase transfer catalyst.

The phase transfer catalyst includes quaternary ammonium salts such as tetra-n-butyl ammonium bromide, benzyl triethyl ammonium chloride, tetra-n-butyl ammonium hydrogen sulfate and trioctyl methyl ammonium chloride, phosphonium salts such as triphenylphosphine bromide, polyether compounds such as 18-crown-6, and polyethylene glycol; etc. Of them, quaternary ammonium salts are preferable, tetra-n-butyl ammonium bromide is more preferable.

The use amount of the phase transfer catalyst is usually 0.01 mol or more, preferably 0.05 to 1 mol with respect to 1 mol of either compound (4) or phenol compound (5) which is used in the smaller amount.

By carrying out the reaction of compound (4) with phenol compound (5) in the presence of an iodine or iodine compound, the reaction can be progressed more smoothly.

The iodine compound includes alkali metal iodides such as potassium iodide, sodium iodide and lithium iodide, potassium iodide is preferable. As iodine and iodine compound, commercially available ones are usually used as they are. Iodine compounds produced by any known methods may also be used.

The use amount of iodine or iodine compound is usually 0.01 mol or more, preferably 0.05 to 1 mol with respect to 1 mol of either compound (4) or phenol compound (5) which is used in the smaller amount.

The reaction temperature is usually −5° C. or more and not more than the boiling point of a solvent, preferably 10 to 100° C. The reaction time is usually 1 to 100 hours.

The reaction may be carried out under normal pressure, or may be carried out under pressure.

The reaction is carried out usually by mixing a compound (4), a phenol compound (5) and a base, and the mixing order of them is not restricted.

The progress of the reaction can be confirmed by usual analysis means such as gas chromatography, high performance liquid chromatography, thin layer chromatography and NMR.

Thus, a reaction mixture containing benzal halide compound (1) is obtained, and for example, the benzal halide compound (1) can be taken out by concentrating the reaction mixture, if necessary after washing with an aqueous solution of an acid. The taken out benzal halide compound (1) may be further purified by usual purification means such as re-crystallization, distillation and column chromatography. The resultant reaction mixture may be used as it is for the above-described reaction with an alcohol compound.

EXAMPLES

The present invention will be described further in detail by examples below, but the present invention is not limited to these examples. The analysis was carried out by a high performance liquid chromatography internal standard method.

Reference Example 1

Into a 500 mL flask, charged was 84 g of 2,5-dimethylphenol and 148 g of 20 wt % sodium hydroxide aqueous solution. The resultant mixture was stirred at 80° C. for 3 hours, then, cooled down to 60° C., to prepare mixture A.

Into another 500 mL flask, charged was 129 g of 2-(chloromethyl)benzal chloride and 8.1 g of tetra-n-butyl ammonium bromide. Into the resultant mixture, the mixture A prepared above was dropped at 60° C. over a period of 3 hours. After completion of dropping, the resultant mixture was stirred at 60° C. for 5 hours.

The resultant reaction mixture was liquid-separated at 60° C., to obtain 192.6 g of coarse 2-(2,5-dimethylphenoxymethyl)benzal chloride. Content: 94.8 wt %.

Example 1

Into a 1000 mL flask, charged was 213 g of ethylene glycol, 65 g of calcium carbonate and the whole amount of the coarse 2-(2,5-dimethylphenoxymethyl)benzal chloride obtained in Reference Example 1. The resultant mixture was kept at 150° C. for 7 hours. The resultant mixture was cooled down to 80° C., then, 127 g of water and 51 g of 35 wt % hydrochloric acid were added.

The resultant mixture was kept at 50° C. for 1 hour. The resultant mixture was liquid-separated. To the resultant organic layer was added 127 g of water and 51 g of 35 wt % hydrochloric acid, and the resultant mixture was kept at 65° C. for 1 hour. The resultant mixture was liquid-separated, to obtain 147.0 g of coarse 2-(2,5-dimethylphenoxymethyl)benzaldehyde. Content: 85.5 wt %. Yield: 87.2% (based on 2-(2,5-dimethylphenoxymethyl)benzal chloride).

Reference Example 2

Into a 500 mL flask, charged was 84 g of 2,5-dimethylphenol, 148 g of 20 wt % sodium hydroxide aqueous solution and 169 g of xylene. The resultant mixture was stirred at 80° C. for 3 hours, then, cooled down to 60° C., to prepare mixture B.

Into another 500 mL flask, charged was 129 g of 2-(chloromethyl)benzal chloride and 8.1 g of tetra-n-butyl ammonium bromide. Into the resultant mixture, the aqueous layer of the mixture B prepared above was dropped at 60° C. over a period of 3 hours. After completion of dropping, the resultant mixture was stirred at the same temperature for 5 hours. The resultant reaction mixture was liquid-separated at 60° C. The resultant organic layer was concentrated under reduced pressure, to obtain 191.6 g of coarse 2-(2,5-dimethylphenoxymethyl)benzal chloride. Content: 96.1 wt %.

Example 2

The same procedure as in Example 1 was carried out excepting that coarse 2-(2,5-dimethylphenoxymethyl)benzal chloride obtained in Reference Example 2 was used instead of coarse 2-(2,5-dimethylphenoxymethyl)benzal chloride obtained in Reference Example 1, in Example 1, thereby obtaining 148.3 g of coarse 2-(2,5-dimethylphenoxymethyl)benzaldehyde. Content: 87.2 wt %. Yield: 89.7% (based on 2-(2,5-dimethylphenoxymethyl)benzal chloride).

Example 3

Into a 1000 mL flask, charged was 213 g of ethylene glycol, 65 g of calcium carbonate and the whole amount of coarse 2-(2,5-dimethylphenoxymethyl)benzal chloride obtained in the same manner as in Reference Example 1, and the resultant mixture was kept at 150° C. for 7 hours. A part of the resultant mixture was purified by silica gel column chromatography (silica gel: manufactured by Wako Pure Chemical Industries, Ltd. "Wakogel (registered trademark) C-300", eluant: ethyl acetate/hexane=1/10), to obtain a colorless transparent liquid of 2-(2,5-dimethylphenoxymethyl)benzaldehyde ethylene glycol acetal.

Thin layer chromatograph (ethyl acetate:hexane=1:10): Rf=0.45

Gas chromatograph mass analysis: 284 (M+), 162, 119, 105, 91 (base)

$^1$H-NMR (CDCl$_3$): δ (ppm) 2.23 (s, 3H), 2.31 (s, 3H), 4.00 to 4.16 (m, 4H), 5.22 (s, 2H), 6.05 (s, 1H), 6.68 to 6.74 (m, 2H), 7.02 to 7.05 (m, 1H), 7.31 to 7.41 (m, 2H), 7.56 to 7.63 (m, 2H)

$^{13}$C-NMR (CDCl$_3$): δ (ppm) 16.3, 21.7, 65.5, 67.2, 102.2, 112.6, 121.3, 124.1, 126.6, 127.9, 128.3, 129.5, 130.7, 135.2, 136.4, 136.8, 157.0

INDUSTRIAL APPLICABILITY

According to the present invention, a benzaldehyde compound which is useful as a production intermediate of a bactericide can be produced with good yield.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method of producing a corresponding acetal compound which comprises reacting a benzal halide compound represented by formula (1)

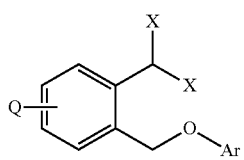

(1)

(wherein, Q represents a hydrogen atom or a halogen atom, X represents a halogen atom, and Ar represents a phenyl group optionally substituted with at least one group selected from the group consisting of alkyl groups having 1 to 4 carbon atoms and halogen atoms) and an alcohol compound in the presence of at least one alkaline earth metal compound selected from the group consisting of alkaline earth metal oxides, alkaline earth metal hydroxides and alkaline earth metal carbonates.

2. The production method according to claim 1, wherein the alcohol compound is a monohydric alcohol compound having 1 to 6 carbon atoms or a dihydric alcohol compound having 2 to 6 carbon atoms.

3. The production method according to claim 1, wherein the alcohol compound is a dihydric alcohol compound having 2 to 6 carbon atoms.

4. The production method according to claim 3, wherein the dihydric alcohol compound is a 1,2-diol compound.

5. The production method according to claim 4, wherein the 1,2-diol compound is ethylene glycol.

6. The production method according to claim 1, wherein the alkaline earth metal is calcium.

7. The production method according to claim 1, wherein the alkaline earth metal compound is an alkaline earth metal carbonate.

8. The production method according to claim 7, wherein the alkaline earth metal carbonate is calcium carbonate.

9. The production method according to claim 1, wherein X represents a chlorine atom.

10. The production method according to claim 1, wherein Ar represents a phenyl group substituted with at least one alkyl group having 1 to 4 carbon atoms.

11. The production method according to claim 10, wherein the phenyl group substituted with at least one alkyl group having 1 to 4 carbon atoms is 2,5-dimethylphenyl group.

12. A method of producing a benzaldehyde compound represented by formula (3)

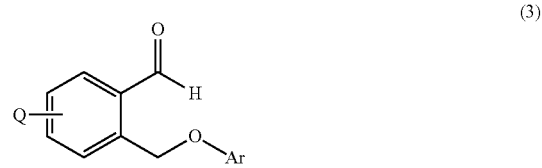

(3)

(wherein, Q and Ar represent respectively the same meaning as described above.) which comprises obtaining an acetal compound by the production method according to claim 1, and reacting the resultant acetal compound and water in the presence of an acid.

13. The production method according to claim 1, wherein the benzal halide compound represented by formula (1) is a benzal halide compound obtained by reacting a compound represented by formula (4)

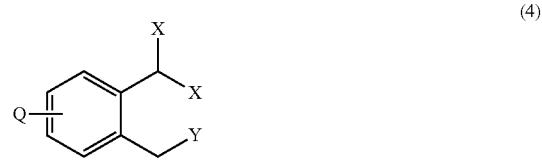

(4)

(wherein, Q and X represent respectively the same meaning as described above, and Y represents a halogen atom.) and a phenol compound represented by formula (5)

Ar—OH     (5)

(wherein, Ar represents the same meaning as described above.) in the presence of a base.

14. 2-(2,5-dimethylphenoxymethyl)benzaldehyde ethylene glycol acetal.

15. The production method according to claim 12, wherein the acid is a Bronsted acid.

16. The production method according to claim 15, wherein the Bronsted acid is hydrochloric acid.

* * * * *

UNITED STATES PATENT AND TRADEMARK OFFICE
CERTIFICATE OF CORRECTION

| | |
|---|---|
| PATENT NO. | : 8,338,625 B2 |
| APPLICATION NO. | : 12/997900 |
| DATED | : December 25, 2012 |
| INVENTOR(S) | : Yoshio Onogawa et al. |

It is certified that error appears in the above-identified patent and that said Letters Patent is hereby corrected as shown below:

On the Title Page:

Delete, "This patent is subject to a terminal disclaimer."

Signed and Sealed this
Fourteenth Day of May, 2013

Teresa Stanek Rea
*Acting Director of the United States Patent and Trademark Office*